United States Patent
Brantley et al.

(10) Patent No.: US 9,274,049 B2
(45) Date of Patent: *Mar. 1, 2016

(54) APPARATUS AND METHODS FOR DETECTING PROPELLANT DEGRADATION IN SOLID PROPELLANT FUEL

(71) Applicant: The United States of America as represented by the Secretary of the Army, Washington, DC (US)

(72) Inventors: Christina L. Brantley, Huntsville, AL (US); Eugene Edwards, Huntsville, AL (US); Paul B. Ruffin, Harvest, AL (US); Fang Luo, State College, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 245 days.

This patent is subject to a terminal disclaimer.

(21) Appl. No.: 14/055,592

(22) Filed: Oct. 16, 2013

(65) Prior Publication Data

US 2014/0246589 A1 Sep. 4, 2014

Related U.S. Application Data

(62) Division of application No. 13/405,469, filed on Feb. 27, 2012, now Pat. No. 8,590,404.

(51) Int. Cl.
*G01N 1/22* (2006.01)
*G01N 21/3504* (2014.01)
*G01J 3/42* (2006.01)
*G01N 33/22* (2006.01)
*G01N 1/24* (2006.01)
*G01N 21/65* (2006.01)
*B82Y 15/00* (2011.01)
(Continued)

(52) U.S. Cl.
CPC ............. *G01N 21/3504* (2013.01); *G01J 3/42* (2013.01); *G01N 1/22* (2013.01); *G01N 1/2202* (2013.01); *G01N 1/2205* (2013.01); *G01N 1/24* (2013.01); *G01N 21/65* (2013.01); *G01N 33/222* (2013.01); *B82Y 15/00* (2013.01); *G01N 2021/3155* (2013.01); *G01N 2021/3595* (2013.01); *Y10T 436/177692* (2015.01); *Y10T 436/178459* (2015.01); *Y10T 436/204998* (2015.01); *Y10T 436/205831* (2015.01)

(58) Field of Classification Search
CPC ........................................................ G01N 1/14
USPC ................... 73/31.05, 31.07, 863.23, 863.51, 73/863.81, 863.83, 864.34, 29.03–29.05, 73/31.04; 55/307, 313, 315, 320, 327, 476
See application file for complete search history.

(56) References Cited

U.S. PATENT DOCUMENTS 5,237,881 A * 8/1993 Ross ................. G01N 1/2258
                                                     55/410
5,297,432 A * 3/1994 Traina .................... G05D 11/03
                                                     73/23.31

(Continued)

*Primary Examiner* — Hezron E Williams
*Assistant Examiner* — Hoang Nguyen
(74) *Attorney, Agent, or Firm* — William B. Haymond (57) ABSTRACT

The present disclosure relates to a gas sensor, including: a gas collecting chamber including: (a) a nanoporous wall including alumina, on a portion of the gas collecting chamber in the near vicinity of the solid propellant fuel; a micro pump attached to the gas collecting chamber; and a gas analysis device connected to the gas collecting chamber. The gas analysis device measures both type and concentration of gases collected in the gas collecting chamber via the nanoporous wall, the gases measured being selected from the group consisting of $CO$, $CO_2$, $NO$, $N_2O$, $NO_2$ and combinations thereof. The present disclosure also relates to a method of sensing propellant degradation in solid fuel and a method of using a gas collecting chamber to sense such degradation.

8 Claims, 6 Drawing Sheets

(51) Int. Cl.
  *G01N 21/31* (2006.01)
  *G01N 21/35* (2014.01)

(56) References Cited

U.S. PATENT DOCUMENTS 5,824,919 A * 10/1998 Hansen .................... G01N 1/22
                                              73/863.12
7,377,188 B2 * 5/2008 Jenkins ................ G01N 1/2205
                                              73/863.23
7,730,796 B2 * 6/2010 Shimada .............. G01N 1/2214
                                              73/863.12
8,087,308 B2 * 1/2012 Gauthier .............. G01N 1/2258
                                              73/863.23
8,146,445 B2 * 4/2012 Ferri .................... G01N 1/2205
                                              73/863.23

* cited by examiner

APPARATUS AND METHODS FOR DETECTING PROPELLANT DEGRADATION IN SOLID PROPELLANT FUEL

This is a divisional application of application Ser. No. 13/405,469 filed on Feb. 27, 2012.

BACKGROUND

Solid propellants (fuels) are widely used in missile engines. The burning of the fuels generates a huge thrust so that a missile can be quickly launched. The main chemical compositions of solid fuels include nitrate ($NO_2$), carbon (C) and sulfur (S). Such fuels are usually stored in the back portion of the missile for effectively generating the thrust.

During the long storage process of the missile (e.g., years), the compositions of the fuels can change due to the slow chemical reaction processes among different components of the fuels as well as the reactions of the fuels with the outside atmosphere (e.g., $O_2$). Thus, to ensure a successful and safe launch of the missile, it is critical to be able to monitor the status of the fuels and ensure a proper fuel composition ratio at the time of use.

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

One method to monitor the status of solid propellant fuel in a rocket is to detect the specific gases generated during the propellant degradation process including, e.g., CO, $CO_2$, NO, $NO_2$, and $N_2O$. The rate of evolution of $NO_2$, for example, is a direct indicator of the available amount of stabilizer that remains in the propellant. As long as the accumulated amount of the detected gases are below certain threshold levels (e.g., several ppm), the fuel is considered to be suitable for use. If the accumulated amount of detected fuel concentrations exceeds the threshold levels, then the fuel needs to be changed prior to use.

To realize the goal of detecting propellant degradation, a gas sensor that can detect types and amounts of multiple gases generated by the degradation of the solid fuel of the missile engine is presented in this disclosure.

The disclosure relates to a high sensitivity/selectivity gas sensor for monitoring propellant degradation. The sensor can simultaneously detect multiple gases (e.g., CO, $CO_2$, NO, $NO_2$, and $N_2O$) emitted due to the propellant degradation. It can therefore be employed to continuously monitor/check the status of the propellant (fuel) of the missile. This is very useful for missile storage and maintenance, as well as for safe and successful launching.

Figure 1:
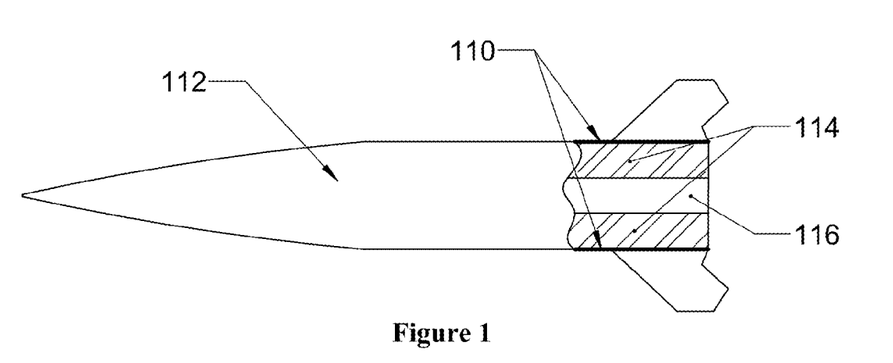
FIG. 1 is a drawing of a cross-section of a missile.

FIG. 1 is a drawing of a missile body 112 with one portion shown in cross-section at the rear of the missile. This cross-sectional portion shows that within a motor casing 110 is the solid propellant fuel 114 with a cylindrical channel 116 down the radial center of the solid propellant fuel 114. In an example, the cylindrical channel 116 is where the gas sensor device of the present application is inserted to sample the gases emitted from the solid propellant fuel 114.

Figure 2:
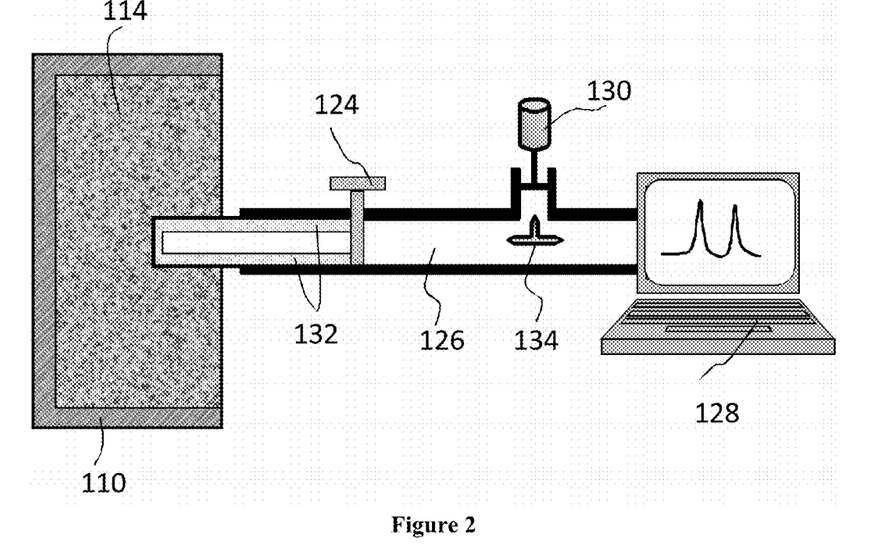
FIG. 2 is a conceptual drawing of a gas sensor for monitoring the status of the solid propellant fuel of the missile engine.

FIG. 2 is a conceptual drawing of an example of the gas sensor for monitoring the propellant degradation. One of the parts of the gas sensor is a gas collecting chamber 126 which includes a portion having a wall 132 made of nanoporous material (e.g., nanoporous alumina ceramics). At least a part of the nanoporous wall 132 of the gas collecting chamber 126 is positioned directly adjacent to the solid propellant fuel 114 which in turn is surrounded by the motor casing 110 of the rocket engine. Another part connected to the gas sensor is a micro pump 130 that can suck the ambient air out of the gas collecting chamber 126, thus forcibly bringing gas into the gas collecting chamber 126 through the pores in the nanoporous wall 132. The micropump 130 can also blow out inert gas (e.g., argon, helium, neon, krypton, xenon, radon, sulfur hexafluoride, nitrogen, and combinations thereof) into the gas collecting chamber 126 and out through the nanoporous wall 132 to rid the nanoporous wall 132 of accumulated particles. As part of the gas collecting chamber 126, there can also be a control valve 124 which can be opened and closed to control the internal pressure of the gas collecting chamber 126. In addition, there is at least one gas analysis device 128 (e.g. FTIR gas spectrometer) which can be connected to the gas collecting chamber 126 to measure the types and the concentration levels of the gases that travel through the nanoporous wall 132 and are collected in the gas collecting chamber 126. As the ambient air is sucked out of the gas collecting chamber 126, gas from the solid propellant fuel 114 can be channeled to the gas analysis device 128 with the help of a baffle 134 located in the gas collecting chamber 126 near the area of the gas collecting chamber 126 where the micro pump 130 is connected.

"Nanoporous" is for the purposes of this disclosure defined as having pores with a diameter roughly in the nanometer range with the pores being as small as $0.2 \times 10^{-9}$ m and as high as $5.0 \times 10^{-4}$ m. Within this range, the nanopore can be large enough to allow gases (such as, e.g., CO, $CO_2$, NO, $NO_2$, and $N_2O$) to pass through it, while it can also be small enough to trap solid propellant particles and keep them from entering into the gas collecting chamber 126.

In an example, the optimum range of mean pore sizes of a nanoporous alumina ceramic material used in the nanoporous wall 132 of the gas collecting chamber 126 is from 200 nm to 300 nm. In another example, the optimum mean pore size is around 250 nm.

The operation of the gas sensing process may be summarized as follows: sucking the gas into the gas collecting chamber 126 through the nanoporous wall 132 by reducing the pressure inside of the gas collecting chamber 126 via the micro pump 130; measuring the concentrations of the gases collected within the gas collecting chamber 126 via at least one gas analysis device 128 from the group including but not limited to devices that measure ultraviolet (UV) absorption spectrum, visible absorption spectrum, IR absorption spectrum, chemical reductions, electrochemical effects, and combinations thereof.

Figure 3:
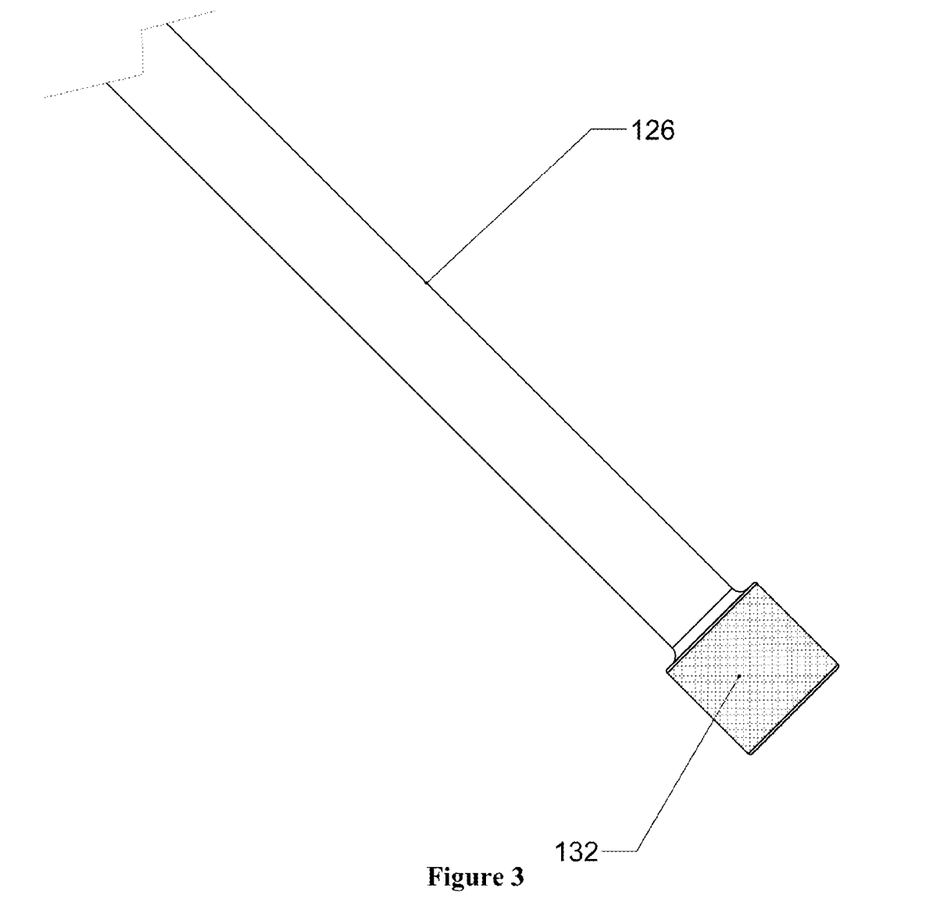
FIG. 3 is a drawing of a gas collecting chamber having an area with a wall made of nanoporous material.

FIG. 3 is a close-up drawing of one example of the gas collecting chamber 126. As shown, the gas collecting chamber 126 has a nanoporous wall 132 surrounding one end of the gas collecting chamber 126. The nanoporous material in the wall 132 includes alumina ($Al_2O_3$). In this example, the inside and outside diameters of an actual chamber like the gas collecting chamber 126 portrayed in FIG. 3 can be around 3 mm and 6 mm, respectively. Alternatively, one example of an analogous, but much smaller version of the gas collecting chamber 126 can be 0.1 mm in internal diameter and 0.5 mm in outside diameter. Such a small gas collecting chamber 126 might be fabricated by, for example, pulsed laser-based micro fabrication.

Figure 4:
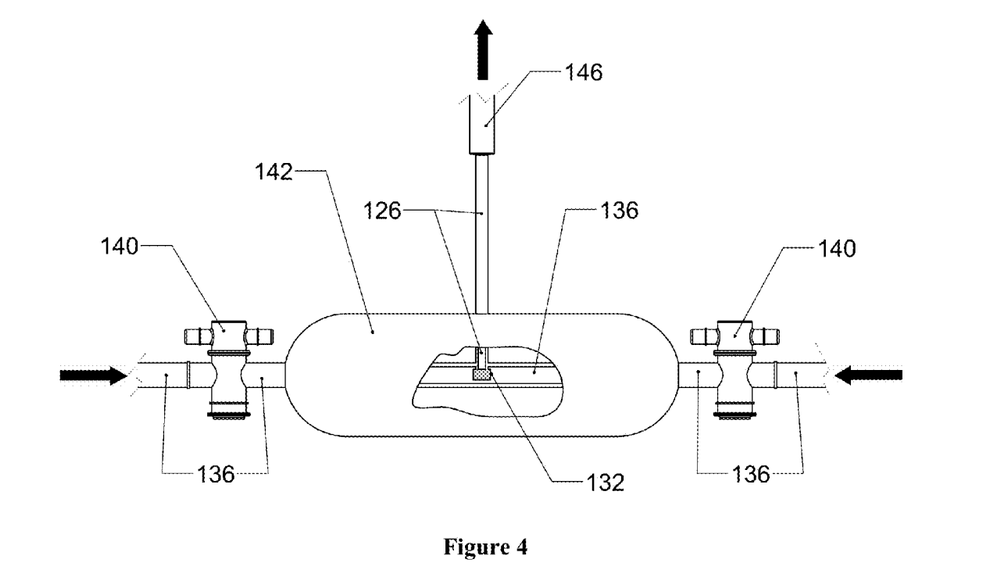
FIG. 4 is a drawing of a gas collecting chamber within a larger chamber.

FIG. 4 is a drawing portraying a device which approximates the gas collecting chamber 126 with its nanoporous wall 132 and its surrounding solid propellant fuel area 114 giving off propellant degradation gases. The area within the large glass chamber 142 approximates the area surrounded by the motor casing 110 of the missile. Along the inner length of the large glass chamber 142, there is a tubular chamber 136 running between two incoming gas valves 140 on each side of the tubular chamber 136. Inserted tightly into the tubular chamber 136 is the nanoporous wall 132 of the gas collecting chamber 126. Extending out from the nanoporous wall 132 in the tubular chamber 136 is the gas collecting chamber 126 which further extends out of the large glass chamber 142. Thus the nanoporous wall 132 is positioned inside the tubular chamber 136 so that gases in the tubular chamber 136 can be sucked out through the nanoporous wall 132 and into the gas collecting chamber 126. In this example, the gas stream going into the tubular chamber 136 is controlled by the two valves 140 on each side of the large glass chamber 142. The two valves 140 are connected to the separate ends of the tubular chamber 136 as the two ends jut out of the large glass chamber 142. The valves 140 can control ingoing gas flow to and outgoing gas flow from the tubular chamber 136. The nanoporous wall 132 of the gas collecting chamber 126 provides a nanoporous filter for the gases to travel through from the tubular chamber 136 into the gas collecting chamber 126 when air is sucked from the gas collecting chamber 126 by means such as the micro pump 130. Consistent with the arrangement of FIG. 4, the micro pump 130 can be connected to the outlet 146.

Figure 5:
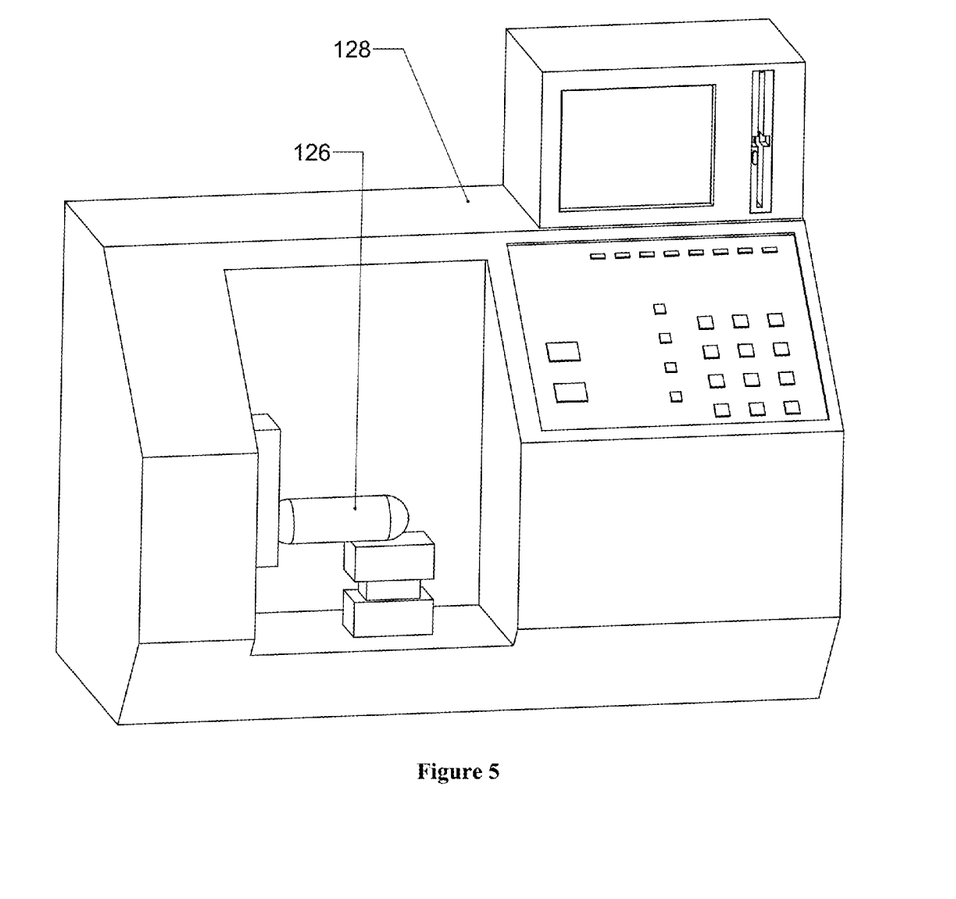
FIG. 5 is a drawing of a Fourier Transform Infrared (FTIR) gas spectrometer used to measure the infrared (IR) absorption spectrum of the gas in a gas collecting chamber.

To measure the concentration of the gas inside the gas collecting chamber 126, the gas travels out through the outgoing gas outlet 146 from the gas collecting chamber 126 to a gas analysis device 128 such as the FTIR gas spectrometer which measures IR absorption spectrum. In some examples, the gas collecting chamber 126 can be detached, transported and attached directly to the gas analysis device 128 such as the FTIR gas spectrometer, as shown in FIG. 5. Specifically, FIG. 5 is a drawing of a gas analysis device 128 (FTIR gas spectrometer) with a gas collecting chamber 126 containing collected gas. The gas collecting chamber 126 is attached to the appropriate portion of the gas analysis device 128 (FTIR gas spectrometer).

The present disclosure relates to a method of sensing propellant degradation in solid propellant fuel 114 as well as a method of using a gas collecting chamber 126 to sense propellant degradation in solid propellant fuel 114. Both methods include the steps of: collecting gas in a near vicinity of the solid propellant fuel 114 into a gas collecting chamber 126, the gas passing through a nanoporous wall 132 including alumina on a portion of the gas collecting chamber 126, the nanoporous wall 132 being positioned near the solid propellant fuel 114, and the collecting of gas being accomplished by reducing internal pressure of the gas collecting chamber 126 via a micro pump 130; and measuring concentrations of gases collected from within the gas collecting chamber 126 via gas sensing methods selected from the group consisting of a UV absorption spectrum measuring method, a visible absorption spectrum measuring method, an IR absorption spectrum measuring method, a chemical reductions measuring method, an electrochemical effects measuring method, and combinations thereof. In a non-limiting example, the gases being measured are selected from the group consisting of CO, $CO_2$, NO, $N_2O$, $NO_2$ and combinations thereof. In another non-limiting example, the nanoporous wall 132 has selectivity for the group of gases consisting of CO, $CO_2$, NO, $N_2O$, $NO_2$ and combinations thereof. In yet another example, the nanoporous wall 132 is comprised of pores having an average diameter of from $0.2 \times 10^{-9}$ m to $5.0 \times 10^{-4}$ m.

In another non-limiting example of the above methods of sensing propellant degradation and using the gas collecting chamber 126, the internal pressure of the gas collecting chamber 126 can vary from 0 to 5,000,000 pounds per square inch. Furthermore, in another example, the pressure of the gas collecting chamber 126 is at least partly regulated by a control valve 124 in the gas collecting chamber 126. The control valve 124 can both open and close the gas collecting chamber 126 to outside gas passing through the nanoporous wall 132.

In yet another non-limiting example of the above methods of sensing propellant degradation and using the gas collecting chamber 126, non-reactive inert gas can be injected into the gas collecting chamber 126 under positive pressure to blow away solid particles lodged in the pores in the nanoporous wall 132. In a further non-limiting example, the inert gas is selected from the group consisting of argon, helium, neon, krypton, xenon, radon, sulfur hexafluoride, nitrogen and combinations thereof.

The present disclosure also relates to a gas sensor. The gas sensor includes: a gas collecting chamber 126. The gas collecting chamber 126 includes a nanoporous wall 132, which includes alumina on a portion of the gas collecting chamber 126 in the near vicinity of the solid propellant fuel 114; a micro pump 130 attached to the gas collecting chamber 126; and a gas analysis device 128 that can be connected to the gas collecting chamber 126. The gas analysis device 128 can measure both type and concentration of gases collected in the gas collecting chamber 126 via the nanoporous wall 132. The gases measured are selected from the group consisting of CO, $CO_2$, NO, $N_2O$, $NO_2$ and combinations thereof. In a non-limiting example, the pores in the nanoporous wall 132 have an average diameter of from $0.2 \times 10^{-9}$ m to $5.0 \times 10^{-4}$ m. In a further non-limiting example, the pores in the nanoporous wall 132 have an average diameter of from 200 nm to 300 nm.

In another non-limiting example of the gas sensor, the gas collecting chamber 126 has an internal pressure varying from 0 to 5,000,000 pounds per square inch. In another example, the gas sensor further comprises a control valve 124 to at least partially regulate the pressure in the gas collecting chamber 126. The control valve 124 can open and close the gas collecting chamber 126 to outside gas.

In still another non-limiting example, the gas analysis device 128 is selected from the group consisting of a UV absorption measuring device, a visible absorption measuring device, an IR absorption measuring device, a Raman effect measuring device, a chemical reductions measuring device, an electrochemical effects measuring device, and combinations thereof.

In yet another non-limiting example, the nanoporous wall 132 further comprises nanoporous material selected from the group consisting of ceramics, polymers, glasses, crystals and combinations thereof.

In still another non-limiting example, the gas collecting chamber 126 is from 100 nm to 1,000 mm in internal diameter.

EXAMPLE

Figure 6:
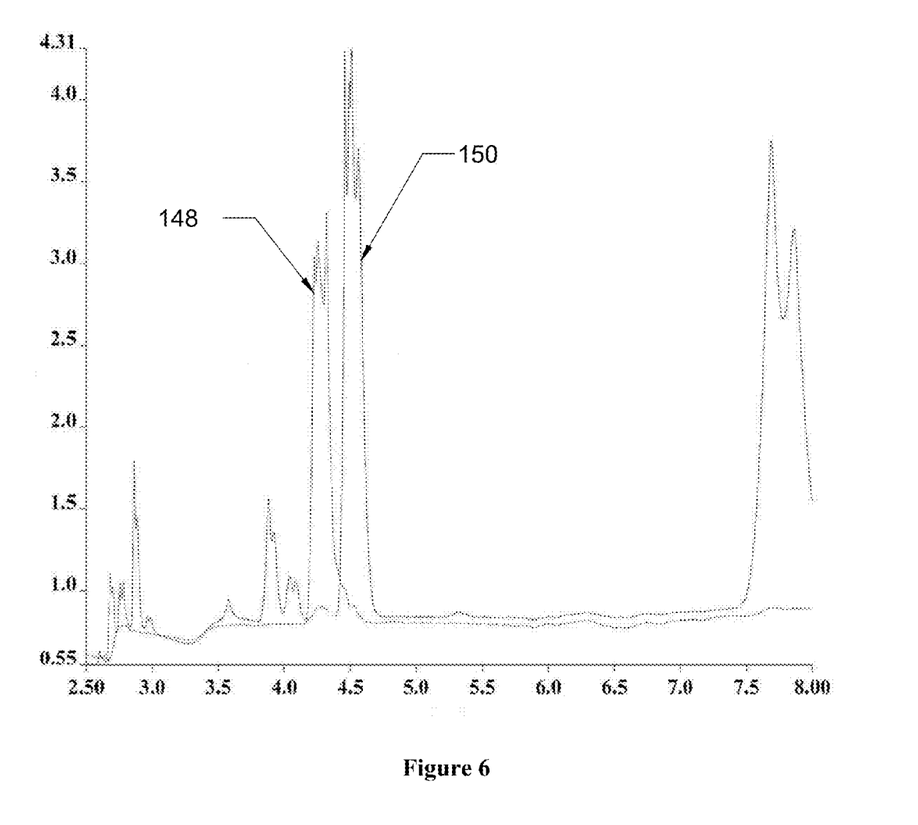
FIG. 6 is a graph depicting the experimentally measured IR absorption of $CO_2$ and $N_2O$ gases in a gas collecting chamber.

Testing was conducted to establish the presence and concentration of (via the IR absorption spectrum) two related gases, $CO_2$ and $N_2O$, by a gas analysis device 128 which is illustrated in FIG. 5. The gas analysis device 128 was connected to the gas collecting chamber 126 having a nanoporous wall 132. The tubular chamber 136 within the large glass chamber 142 contained the two types of gases. The gases were then collected in the gas collecting chamber 126 by reducing internal pressure of the gas collecting chamber 126 via a micro pump 130 and forcing gas in the tubular chamber 136 through the ceramic alumina nanoporous wall 132 and into the gas collecting chamber 126. FIG. 6 shows the experimentally measured IR absorption spectrum obtained by the gas analysis device 128 (FTIR gas spectrometer). The y axis tracks absorption units and the x axis tracks wavelength in nanometers. FIG. 6 clearly shows a major $CO_2$ peak 148 and a major $N_2O$ peak 150 in the IR absorption spectrum obtained by the gas analysis device 128.

While several embodiments have been described in detail, it will be apparent to those skilled in the art that the disclosed embodiments may be modified. Therefore, the foregoing description is to be considered exemplary rather than limiting.

What is claimed is:

1. A method of sensing propellant degradation in solid propellant fuel, comprising the steps of:
   collecting gas in a near vicinity of the solid propellant fuel into a gas collecting chamber, the gas passing through a nanoporous wall including alumina on a portion of the gas collecting chamber, the nanoporous wall being positioned near the solid propellant fuel, and the collecting of gas being accomplished by a) reducing internal pressure of the gas collecting chamber via a micro pump for sucking ambient air out of the gas collecting chamber thereby forcibly bringing gas out of the gas collecting chamber through the pores in the nanoporous wall and also for blowing inert gas selected from a group consisting of argon, helium, neon, krypton, xenon, radon, sulfur hexafluoride, nitrogen and combinations thereof into the gas collecting chamber and out through the nanoporous wall thereby to rid the nanoporous wall of accumulated particles, and by b) channeling the gas sucked by the micro pump from the solid propellant fuel to the gas analysis device via a baffle, the baffle being located in the gas collecting chamber near an area of the gas collecting chamber where the pump is connected; and
   measuring concentrations of gases collected within the gas collecting chamber via gas sensing methods selected from a group consisting of an ultraviolet absorption spectrum measuring method, a visible absorption spectrum measuring method, an infrared absorption spectrum measuring method, a chemical reductions measuring method, an electrochemical effects measuring method, and combinations thereof, the gases measured being selected from a group consisting of CO, $CO_2$, NO, $N_2O$, $NO_2$ and combinations thereof.

2. The method according to claim 1, wherein nanoporous material in the nanoporous wall comprises pores having an average diameter of from $0.2 \times 10^{-9}$ m to $5.0 \times 10^{-4}$ m.

3. The method according to claim 1, wherein the gas collecting chamber has an internal pressure varying from 0 to 5,000,000 pounds per square inch.

4. The method according to claim 3, wherein the pressure of the gas collecting chamber is at least partly regulated by a control valve in the gas collecting chamber, the control valve either opening or closing the gas collecting chamber to incoming outside gas.

5. A method of using a gas collecting chamber to sense propellant degradation in solid propellant fuel, comprising the steps of:
   collecting gas in a near vicinity of the solid propellant fuel into the gas collecting chamber, the gas passing through a nanoporous wall including alumina on a portion of the gas collecting chamber, the nanoporous wall being positioned near the solid propellant fuel, and the collecting of gas being accomplished by a) reducing internal pressure of the gas collecting chamber via a micro pump for sucking ambient air out of the gas collecting chamber thereby forcibly bringing gas out of the gas collecting chamber through the pores in the nanoporous wall and also for blowing inert gas selected from a group consisting of argon, helium, neon, krypton, xenon, radon, sulfur hexafluoride, nitrogen and combinations thereof into the gas collecting chamber and out through the nanoporous wall thereby to rid the nanoporous wall of accumulated particles, and by b) channeling the gas sucked by the micro pump from the solid propellant fuel to the gas analysis device via a baffle, the baffle being located in the gas collecting chamber near an area of the gas collecting chamber where the pump is connected; and
   measuring concentrations of gases collected within the gas collecting chamber via gas sensing methods selected from a group consisting of an ultraviolet absorption spectrum measuring method, a visible absorption spectrum measuring method, an infrared absorption spectrum measuring method, a chemical reductions measuring method, an electrochemical effects measuring method, and combinations thereof, the gases measured being selected from a group consisting of CO, $CO_2$, NO, $N_2O$, $NO_2$ and combinations thereof.

6. The method according to claim 5, wherein nanoporous material in the nanoporous wall comprises pores having an average diameter of from $0.2 \times 10^{-9}$ m to $5.0 \times 10^{-4}$ m.

7. The method according to claim 5, wherein the gas collecting chamber has an internal pressure varying from 0 to 5,000,000 pounds per square inch.

8. The method according to claim 7, wherein the pressure of the gas collecting chamber is at least partly regulated by a control valve in the gas collecting chamber, the control valve either opening or closing the gas collecting chamber to incoming outside gas.

* * * * *